United States Patent
Kumar et al.

(10) Patent No.: US 7,452,074 B2
(45) Date of Patent: Nov. 18, 2008

(54) OPTICAL ELEMENTS AND METHOD OF MAKING THE SAME USING LIQUID CRYSTAL MATERIALS

(75) Inventors: Anil Kumar, Murrysville, PA (US); Peter C. Foller, Murrysville, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 110 days.

(21) Appl. No.: 11/527,131

(22) Filed: Sep. 26, 2006

(65) Prior Publication Data

US 2007/0076167 A1 Apr. 5, 2007

Related U.S. Application Data

(60) Provisional application No. 60/720,923, filed on Sep. 27, 2005.

(51) Int. Cl.
*G02C 7/02* (2006.01)
(52) U.S. Cl. ........................................... 351/159
(58) Field of Classification Search ......... 351/159–176; 359/652
See application file for complete search history.

(56) References Cited

U.S. PATENT DOCUMENTS

| | | |
|---|---|---|
| 6,761,454 B2 | 7/2004 | Lai et al. |
| 6,781,681 B2 | 8/2004 | Horwitz |
| 6,813,082 B2 | 11/2004 | Bruns |
| 6,851,805 B2 * | 2/2005 | Blum et al. ............. 351/160 R |
| 7,108,954 B2 | 9/2006 | Nishimura et al. |
| 2003/0081172 A1* | 5/2003 | Dreher ....................... 351/176 |
| 2004/0160574 A1 | 8/2004 | Dreher |

FOREIGN PATENT DOCUMENTS

| | | |
|---|---|---|
| WO | WO 97/42530 | 11/1997 |
| WO | WO 02/28272 A1 | 4/2002 |
| WO | WO 2004/015481 A1 | 2/2004 |

OTHER PUBLICATIONS

Paul c. Hiemenz, *Polymer Chemistry*, Marcel Dekker, Inc., (1984) p. 7.

* cited by examiner

*Primary Examiner*—Darryl J Collins
(74) *Attorney, Agent, or Firm*—Deborah M. Altman; Linda Pingitore

(57) ABSTRACT

Provided is a method for making a customized lens including applying a customizable material onto a surface of an ophthalmic substrate; and writing index-change information to the material to form a variable-index layer on the substrate surface. Also provided is a customized ophthalmic element including an ophthalmic substrate; and a variable-index layer of a liquid crystal material connected to at least a portion of the substrate. Further provided is an ophthalmic element having a pair of complementary substrates, each of which has a complementary surface and being positioned such that their complementary surfaces are spaced apart and facing each other, an alignment layer of a patterned alignment material connected to at least one of the complementary surfaces of the pair of substrates, and a variable-index coating interposed between the pair of substrates, such that the liquid crystal material of the variable-index coating is aligned with the patterned alignment material.

5 Claims, 1 Drawing Sheet

OPTICAL ELEMENTS AND METHOD OF MAKING THE SAME USING LIQUID CRYSTAL MATERIALS

CROSS REFERENCE TO RELATED APPLICATIONS

This application claims the benefit of priority of U.S. Provisional Patent Application No. 60/720,923, filed Sep. 27, 2005.

BACKGROUND

The present disclosure generally relates to methods of preparing customized optical elements, and in particular customized ophthalmic elements, coating compositions for customized optical elements and customized optical elements made using the same. For example, various non-limiting embodiments disclosed herein relate to customized ophthalmic elements and methods of forming customized ophthalmic elements using thousands of points of refraction data (or "prescription information") obtained from a patient's eyes using a wavefront aberrometer. More particularly, certain non-limiting embodiments relate to methods of forming customized ophthalmic elements using a variable index-coating into which index-change information has been written and customized ophthalmic elements so made.

The advent of wavefront aberrometer technology, which maps the optics of the eye over many thousands of points, has allowed for the development of new vision correction technologies that can utilize this digital prescription information. See, for example, U.S. Pat. Nos. 6,813,082, 6,781,681, 6,761,454 & WO 02/28272 which generally disclose systems and methods for using wavefront sensing to determine the objective refraction of a human eye. Until recently, the higher order aberrations could not be measured via conventional refraction equipment. However, commercial refractometers using wavefront aberrometer technology to measure higher order aberrations have been developed, and are now commonly used, for example, to guide laser eye surgery.

A wavefront aberrometer works by using a laser beam, or other light source, to generate a well defined, ordered array of light and dark points. The array of light and dark points is then directed into the patient's eye, and the reflected beam that has been distorted by all optical components of the eye is detected by a wavefront analyzer (a position sensitive device), which digitally maps out these distortions. The distorted array obtained from the patient's eye is compared to a distortion-free array (i.e., one that would be produced by a perfect lens). Using well-defined mathematics (Zernike polynomials), the position of each point in the array is located and the deviations of each point from that of a distortion-free array are calculated. Since these deviations provide information regarding the higher order aberrations of the patient's eye, using the deviation information, a prescription necessary to correct for higher order aberrations can be calculated.

Typical ophthalmic lenses, however, correct only for low order aberration such as tilt (prism), defocus (sphere), and astigmatism (cylinder). Higher order aberrations, such as coma, trefoil and secondary astigmatism, are usually not corrected since these aberrations tend to be patient-specific and current large-scale manufacturing techniques for ophthalmic lenses (such as casting and surfacing) are not well-suited to handle the required customization. Higher order aberrations are thought to correspond to about 20% of the vision correction required by most people. By correcting these higher order vision aberrations, better than 20/20 vision correction (or "supervision") may be achievable.

Accordingly, it would be advantageous to provide customized ophthalmic elements, which may be used to correct a variety of vision deficiencies, and methods of forming the same. Further, it would be advantageous to provide a method of forming a customized ophthalmic element by customizing a standard ophthalmic substrate, such as a standard single or multi-vision lens, a contact lens or lens blank, to create a customized lens that corrects higher order aberration(s). Still further, it would be advantageous to provide methods of forming customized ophthalmic elements that may be used to convert a standard ophthalmic substrate into a bi-focal, tri-focal or multi-focal lens, with or without higher order aberration correction.

BRIEF SUMMARY OF THE DRAWINGS

Aspects of the present disclosure may be better understood when read in conjunction with the drawings in which.

SUMMARY OF THE INVENTION

Figure 1:
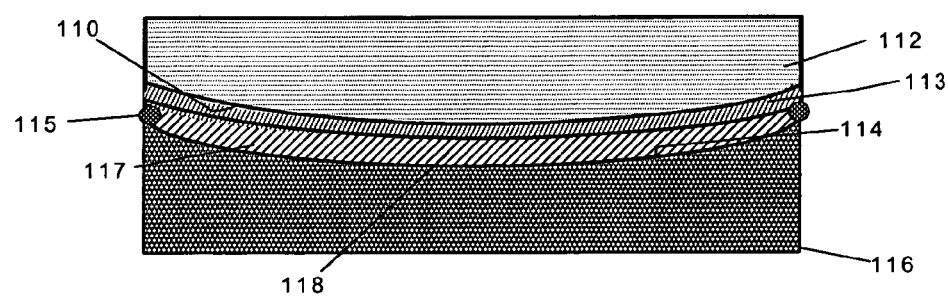
FIG. 1 is a schematic, cross-sectional view of an overmolding assembly that may be used in accordance with one non-limiting embodiment disclosed herein.
Figure 2:
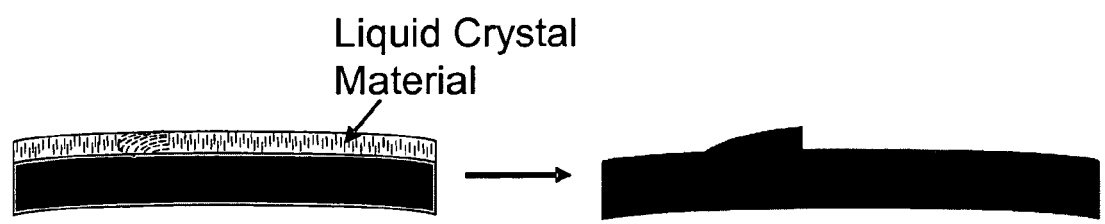
FIG. 2 is a schematic illustration showing both a smooth-faced bifocal lens according to one non-limiting embodiment of the invention and a conventional bifocal lens.

The present invention is directed to a method for making a customized lens comprising: applying a customizable material onto a surface of an ophthalmic substrate; and writing index-change information to the customizable material to form a variable index layer on the ophthalmic substrate surface.

The present invention also is directed to a customized ophthalmic element comprising an ophthalmic substrate; and a variable-index layer comprising a liquid crystal material connected to at least a portion of the substrate.

Also provided is an ophthalmic element comprising a pair of complementary ophthalmic substrates, each of the substrates having a complementary surface, the pair of complementary ophthalmic substrates being positioned such that their complementary surfaces that are spaced apart and facing each other, an alignment layer comprising an at least partial coating of a patterned alignment material connected to at least of portion of at least one of the complementary surfaces of the pair of ophthalmic substrates, and a variable-index coating comprising a liquid crystal material that is interposed between the pair of ophthalmic substrates. At least a portion of the liquid crystal material of the variable-index coating is aligned with at least a portion of the patterned alignment material.

DETAILED DESCRIPTION OF VARIOUS NON-LIMITING EMBODIMENTS OF THE INVENTION

As used in this specification and the appended claims, the singular forms "a," "an," and "the" include plural referents unless expressly and unequivocally limited to one referent. For the purposes of this specification, unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification are approximations that may vary depending upon the desired properties sought to be obtained by the present invention. At the very least, and not as an attempt to limit the application of the doctrine of equivalents, each numerical parameter should at least be construed in light of the number of reported significant digits and by applying ordinary rounding techniques.

All numerical ranges herein include all numerical values and ranges of all numerical values within the recited numerical ranges. Notwithstanding that the numerical ranges and parameters setting forth the broad scope of the invention are approximations, the numerical values set forth in the specific examples are reported as precisely as possible. However, it should be appreciated that any numerical value, inherently contains certain errors necessarily resulting from the standard deviation found in their respective testing measurements.

The present disclosure describes several different features and aspects of the invention with reference to various exemplary embodiments. It is understood, however, that the invention embraces numerous alternative embodiments, which may be accomplished by combining any of the different features, aspects, and embodiments described herein in any combination that one of ordinary skill in the art would find useful. Various non-limiting embodiments disclosed herein provide a method of making a customized lens comprising applying a customizable material onto the surface of a ophthalmic substrate (e.g., a standard lens or lens blank), and "writing" index-change information based on prescription information obtained from a patient's eye to the customizable material to create a variable-index layer. The variable-index layer may correct for higher order aberrations and/or may provide for multiple focal points within the ophthalmic substrate (e.g., bi-focal, tri-focal or multi-focal lenses). After forming the variable-index layer, the layer may be at least partially set to "lock in" the index-change information. Optionally, one or more protective coatings may be applied over the variable-index coating and at least partially set. The variable-index layer can be in the form of a coating or in the form of a film or sheet, as discussed below.

As used herein, the following terms have the following meanings. The term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intraocular lenses, magnifying lenses, and protective lenses or visors. The term "ophthalmic substrate" means a component useful in forming an ophthalmic element. The term "customizable material" means a substance that can be modified or adapted to display variations in refractive index. The term "index-change information" means data related to positional variations in refractive index. The terms "write", "writing", "written" or terms of like import refer to the transfer of information. Further "writing" may involve the direct transfer of information from one medium to another or it may involve the indirect transfer of information through some intermediate channel or medium. For example, although not limiting herein, according to one non-limiting embodiment, index-change information may be transferred (i.e., written) directly from a wavefront aberrometer (or other memory device in which such information is stored) into the customizable material that is applied to the surface of the ophthalmic substrate. Alternatively, according to another non-limiting embodiment disclosed herein, index-change information may be transferred (i.e., written) from a wavefront aberrometer (or other memory device in which such information is stored) into an alignment material that is applied to the surface of an ophthalmic substrate or mold, and thereafter the index-change information may be transferred (i.e., written) from the alignment material to the customizable material that is applied over the alignment material. As used herein to modify the terms coating, film or sheet, the term "variable-index" means displaying variations in refractive index. Thus, a "variable-index coating" is a coating that displays variations in refractive index. The terms "set" and "setting" (and like terms) include, without limitation, curing, polymerizing, cross-linking, cooling, and drying (which may included removal of water or another solvent).

According to various non-limiting embodiments disclosed herein, the ophthalmic substrate may be a standard ophthalmic lens substrate, for example, a stock semi-finished single vision or finished single vision lens made from glass or a polymer, such as polycarbonate or CR-39® monomer, and may further comprise one or more coatings, such as but not limited to, abrasion resistant coatings, tie-layer coatings, tinted coatings, anti-reflective coatings, polarizing coatings, photochromic coatings, and primer coatings on a surface thereof. According to other non-limiting embodiments, the ophthalmic substrate may be a lens blank or a semi-finished or finished multi-vision lens. According to still other non-limiting embodiments, the ophthalmic substrate may be a contact lens, for example, a contact lens formed from hydroxyethyl-methacrylate (or "HEMA"). Further, as discussed below in more detail, according to certain non-limiting embodiments disclosed herein, the ophthalmic substrate may be a pre-formed substrate that is formed prior to customization, or the ophthalmic substrate may be customized when it is formed.

As discussed above, according various non-limiting embodiments disclosed herein, index-change information is written to a customizable material. According to one non-limiting embodiment, the customizable material may comprise a liquid crystal material (i.e., a material comprising at least one liquid crystal mesogen) and/or a self-assembling material, at least a portion of which is capable of being ordered. As used herein the term "order" means bring into a suitable arrangement or position, such as aligning with another structure or material, or by some other force or effect. Thus, as used herein the term "order" encompasses both contact methods of ordering a material, such as by aligning with another structure or material, and non-contact methods of ordering a material, such as by exposure to an external force or effect. The term "order" also encompasses combinations of contact and non-contact methods. As used herein the term "align" means to bring into suitable arrangement or position by interaction with another material, compound or structure.

Examples of liquid crystal materials that are suitable for use in connection with various non-limiting embodiments disclosed herein include, without limitation, mono- as well as multi-functional liquid crystal monomers, oligomers (i.e., materials containing from 2 to 10 repeat units) or polymers (i.e., materials containing more than 10 repeat units). See for example, Paul Hiemenz, *Polymer Chemistry*, Dekker (1984) at page 7, which is hereby specifically incorporated by reference herein. Although not required, the liquid crystal monomers, oligomers or polymers may be cross-linkable liquid crystal monomers, oligomers or polymers, and further may be photo cross-linkable liquid crystal monomers, oligomers or polymers. Non-limiting examples of cross-linkable liquid crystal monomers, oligomers or polymers suitable for use include liquid crystal monomers, oligomers or polymers having functional groups comprising acrylate, methacrylate, allyl, allyl ethers, alkynes, amino, melamines, anhydrides, epoxy, hydroxyl, isocyanates, blocked isocyanates, siloxanes, thiocyanates, thiols, urea, vinyl, vinyl ether, acid, ester, hydrosilanes, mixtures thereof, or combinations thereof.

Liquid crystal mesogens are known to have refractive indices that vary with respect to their long axes. However, while a single liquid crystal mesogen displays refractive index anisotropy, if the mesogens of the liquid crystal material are not suitably positioned or arranged, no net refractive index change will be observed for the liquid crystal material as a whole. That is, due to the random positioning of the mesogens of the liquid crystal material, no net or overall change in refractive index of the liquid crystal material as a whole will be observed. Therefore, it is generally necessary to suitably position or arrange the mesogens of the liquid crystal material in order to achieve the desired change in refractive index ("Δn") within the liquid crystal material as a whole. However, it should be appreciated that in order to achieve the desired overall refractive index change within a liquid crystal material or portion thereof, it is not necessary that all of the mesogens of the liquid crystal material or portion thereof be aligned or ordered in exactly the same direction, and that variations in positioning of the individual mesogens is permissible and may occur provided that the desired optical properties are achieved within the liquid crystal material or portion thereof.

Typical liquid crystal materials have an Δn value that varies from 0.01 to 0.3. Liquid crystal materials with an Δn ranging greater than 0.3 to 0.7 are known in the literature and can be synthesized. Liquid crystal materials having □n values greater than 0.7 to 1.0 or more are theoretically possible and include liquid crystal materials containing liquid crystal mesogens having a highly polarizable electron density (i.e., materials with a high electronic polarizability). Liquid crystal materials suitable for use in the present invention can have Δn values ranging between any of the above-recited values, including the recited values. For example, suitable liquid crystal materials can have Δn values ranging from 0.01 to 1.0.

Non-limiting examples of suitable liquid crystal materials include liquid crystal materials (i.e., monomers, oligomers, and/or polymers) represented by:

L-[S$_1$]$_w$-[A$_1$-[S$_2$]$_x$]$_{x'}$-[A$_2$-[S$_3$]$_y$]$_{y'}$-[A$_3$-[S$_4$]$_z$]$_{z'}$-S$_5$-L wherein:
(a) each A$_1$, A$_2$, and A$_3$ is independently chosen for each occurrence from
  (i) —C≡C—; and
  (ii) divalent group, said divalent group being an unsubstituted or a substituted aromatic group, an unsubstituted or a substituted alicyclic group, an unsubstituted or a substituted heterocyclic group or a mixture thereof, wherein the aromatic, alicyclic, and heterocyclic substituents are independently halogen, C$_1$-C$_{18}$ alkoxy, poly(C$_1$-C$_{18}$ alkoxy), amino, amino(C$_1$-C$_{18}$) alkylene, C$_1$-C$_{18}$ alkylamino, di-(C$_1$-C$_{18}$)alkylamino, C$_1$-C$_{18}$ alkyl, C$_2$-C$_{18}$ alkene, C$_2$-C$_{18}$ alkyne, C$_1$-C$_{18}$alkyl(C$_1$-C$_{18}$)alkoxy, C$_1$-C$_{18}$ alkoxycarbonyl, C$_1$-C$_{18}$ alkylcarbonyl, carbonate, acetyl, C$_3$-C$_{10}$ cycloalkyl, C$_3$-C$_{10}$ cycloalkoxy, isocyanato, amido, cyano, nitro, a straight-chain or branched C$_1$-C$_{18}$ alkyl group that is mono-substituted with cyano, halo or C$_1$-C$_{18}$ alkoxy or that is poly-substituted with halo, or a group represented by the following formulae:

-M(T)$_{(t-1)}$

-M(OT)$_{(t-1)}$ wherein M is aluminum, antimony, tantalum, titanium, zirconium or silicon, T is an organofunctional radical, an organofunctional hydrocarbon radical, an aliphatic hydrocarbon radical or an aromatic hydrocarbon radical, and t is the valence of M;

(b) w, x, y, and z are each independently 0, 1, 2, 3 or 4;

(c) each S$_1$, S$_2$, S$_3$, S$_4$, and S$_5$ is independently chosen for each occurrence from a spacer unit chosen from a single bond, —(CH$_2$)$_r$—, —(CF$_2$)$_p$—, —Si(CH$_2$)$_r$—, —(Si[(CH$_3$)$_2$]O)$_p$—, —O—, —CO—, —NR'—, —CR'=CR'—, —C—C—, —N=N—, a straight-chain or branched C$_1$-C$_{24}$ alkylene residue, said C$_1$-C$_{24}$ alkylene residue being unsubstituted, mono-substituted by cyano or halo or poly-substituted by halo, "r" ranges from 1 to 20 (inclusive), "p" is a whole number ranging from 1 to 16 (inclusive); each R' is independently chosen from hydrogen, C$_1$-C$_6$ alkyl, cycloalkyl and aryl; provided that when two spacer units comprising heteroatoms are linked together the spacer units are link so that heteroatoms are not directly linked to each other;

(d) each L is independently hydrogen, halogen, carboxyl, hydroxy, aryl, alkyl, alkoxy, amine, analkylamino, alkylalkoxy, alkoxyalkoxy, polyalkyl ether, (C$_1$-C$_6$)alkyl (C$_1$-C$_6$)alkoxy(C$_1$-C$_6$)alkyl, polyethyleneoxy, polypropyleneoxy, ethylene, acrylate, methacrylate, 2-chloroacrylate, 2-phenylacrylate, acryloylphenylene, acrylamide, methacrylamide, 2-chloroacrylamide, 2-phenylacrylamide, epoxy, isocyanate, thioisocyanate, itaconic acid ester, vinyl ether, vinyl ester, a styrene derivative, oxetane, succinamide, siloxane, an ethyleneimine derivative, a maleic acid derivative, a fumaric acid derivative, an unsubstituted cinnamic acid derivative, a cinnamic acid derivative that is substituted with one or more substituents chosen from methyl, methoxy, cyano and halogen, or a substituted or unsubstituted chiral or non-chiral monovalent or divalent group, said chiral or non-chiral group being a steroid radical, a terpenoid radical, an alkaloid radical or a mixture thereof, provided that if the chiral or non-chiral group is substituted, at least one substituent is an alkyl group having an optically active group, an alkoxy group, an amino group, a cycloalkyl group, an alkylalkoxy group, a fluoroalkyl group, a cyanoalkyl group, a cyanoalkoxy group or a mixture thereof; and (e) x', y' and z' are each independently 0, 1, 2, 3 or 4.

Some specific non-limiting examples of liquid crystal materials that may provide Δn values ranging from greater than 0.3 to 0.7 include liquid crystal materials represented by:

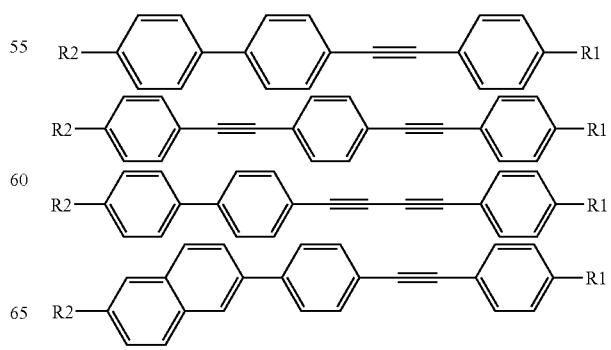

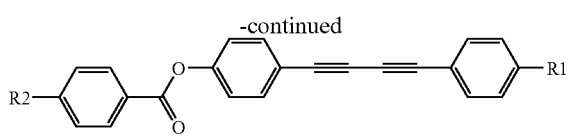
-continued wherein R1 and R2 are groups represented by [S]-L and L-[S] respectively, wherein "L" is as defined above and each "S" may be independently selected from the groups set forth above for $S_1$-$S_5$.

One method of ordering the mesogens of a liquid crystal material to obtain a homogenous (planar), homeotropic (vertical) and/or tilted arrangement of the mesogens is surface-induced alignment. For example, liquid crystal monomers (i.e., monomers containing at least one liquid crystal mesogen) can align with a pattern written to an alignment layer with which the liquid crystal monomer is in contact. Alternatively, a field-induced orientation process (e.g., using an electrical or magnetic field) and/or a photo-induced orientation processes (e.g., using electromagnetic radiation) may be used to order liquid crystal mesogens in a variety of patterns, either with or without the use of an alignment layer.

According to various non-limiting embodiments disclosed herein, the alignment layer may induce homogeneous alignment of a liquid crystal material that is in contact therewith, homeotropic alignment of a liquid crystal material that is in contact therewith, tilted alignment of a liquid crystal material that is in contact therewith or a mixture thereof. For example, the alignment layer according to various non-limiting embodiments disclosed herein may comprise one or more discrete regions wherein homogeneous alignment is induced, one or more discrete regions wherein homeotropic alignment is induced, and one or more discrete regions of wherein tilted alignment is induced.

As used herein the terms "homogeneous arrangement" and "homogeneous alignment" refer to positioning of a liquid crystal material on a surface such that the tilt angle of the liquid crystal material is approximately 0° (including complementary angles thereof). As used herein the term "tilt angle" refers to the average angle formed between the major or long axes of the liquid crystal mesogens of the liquid crystal material and the plane of a surface on which they are ordered. Thus, a homogeneous alignment layer can induce homogeneous alignment of a liquid crystal material that is in contact therewith.

As used herein the terms "homeotropic arrangement" and "homeotropic alignment" refers to positioning of a liquid crystal material on a surface such that the tilt angle of the liquid crystal material is approximately 90° (including complementary angles thereof). Thus, a homeotropically aligned liquid crystal material is a liquid crystal material having an essentially vertical arrangement of mesogens with respect to an alignment surface or layer.

Further, as used herein the term "tilted arrangement" and "tilted alignment" refers to positioning of a liquid crystal material on a surface such that the tilt angle of the liquid crystal material ranges from greater than 0° to less than 90° (including complementary angles thereof).

Non-limiting examples of alignment materials that can be used to form alignment layers according to various non-limiting embodiments disclosed herein include, but are not limited to surfactants, such as alkyl quaternary ammonium salts, L-α-phophatidylocholine (commonly known as "lecithin"), octadecyltriethoxysilane ("ODSE"), high-tilt angle polyimide materials, Langmuir-Blodgett films, deposited oxides, rubbed-orientation materials and photo-orientation materials. As used herein the term "photo-orientation material" means a material that is capable of being ordered using radiation. Non-limiting examples of photo-orientation materials that may be used in connection with various non-limiting embodiments disclosed herein include photo-orientable polymer networks. Specific non-limiting examples of photo-orientable polymer networks include azobenzene derivatives, cinnamic acid derivatives, coumarine derivatives, ferulic acid derivatives and polyimides. Specific non-limiting examples of cinnamic acid derivatives that may be used include polyvinyl cinnamate and polyvinyl esters of paramethoxy cinnamic acid. As used herein the term "rubbed-orientation material" refers to a material that is capable of being ordered by rubbing or by another suitable mechanical process (such as, but not limited to, nano- or micro-lithographic techniques). For example, although not limiting herein, in one non-limiting embodiment, the rubbed-orientation material may be rubbed with a suitably textured cloth, a velvet brush, a spinning ball or stylus. Non-limiting examples of rubbed-orientation materials may be used to form an alignment layer according to various non-limiting embodiments disclosed herein include surfactants, polyimides, polysiloxanes, polyacrylates, polyvinyl alcohols, and polycoumarines. For example, according to one non-limiting embodiment, the rubbed-orientation material may be polyimide that has been rubbed with velvet or a cloth so as to write the desired pattern on at least a portion of the surface of the polyimide.

According to one non-limiting embodiment wherein the customizable material comprises a liquid crystal material, index-change information may be written to the liquid crystal material by surface-induced alignment using an alignment layer formed from a photo-orientation material. For example, according to this non-limiting embodiment, a photo-orientation material may be applied on surface of an ophthalmic substrate and either sequentially or simultaneously ordered and cross-linked by scanning a polarized light over the photo-orientation material to write the index-change information the photo-orientation material. By varying the incident angle of the polarization light with respect to the surface of the ophthalmic substrate in discrete regions or spots on the surface, the orientation of the photo-orientation material can be altered in those regions or spots. The specific spots on the ophthalmic substrate and the incident angles to be used are determined by the pattern calculated from the aberrometer measurements and are based on the prescription information obtained from the patient's eye. Non-limiting examples of polarized light that may be used to write index-change information to a photo-orientation material according to various non-limiting embodiments disclosed herein include use of UV light, visible light, infrared light and combinations thereof. For example, according to one non-limiting embodiment, the polarized light source may be a polarized UV light source. According to another non-limiting embodiment, the polarized light source may be a polarized infrared laser. Further according to various non-limiting embodiments, index-change information may be written to the photo-orientation material using a polarized electron beam.

According to another non-limiting embodiment wherein the customizable material comprises a liquid crystal material, index-change information may be written to the liquid crystal material by surface-induced alignment using an alignment layer formed from an alignment material that has been selectively exposed to electromagnetic radiation of varying energies. For example, according to one non-limiting embodiment, an alignment material, such as, but not limited to, polyimide, may be applied to the surface of an ophthalmic substrate and an electromagnetic radiation source can be scanned over the alignment material to write the index-change information to the alignment material. According to this non-limiting embodiment, by varying the energy of the electromagnetic radiation source with respect to the surface of the ophthalmic substrate in discrete regions or spots on the surface, the degree of polymerization of the polyimide can be altered in those regions or spots, for example by locally forming and/or breaking bonds within the polyimide. Since the orientation of the polyimide molecules in a particular region or spot is related to the degree of polymerization of the polyimide in that region or spot, by selectively altering the degree of polymerization in this manner, index-change information can be transferred to the alignment material. The specific spots on the ophthalmic substrate and the energies employed are determined based on the pattern calculated from the aberrometer measurements, which as previously discussed, is based on the prescription information obtained from the patient's eye.

According another non-limiting embodiment, an alignment layer comprising a surfactant may be applied to the surface of an ophthalmic substrate and an electromagnetic radiation source can be scanned over the alignment material to write the index-change information to the alignment material. According to this embodiment, by varying the energy of the electromagnetic radiation source with respect to the surface of the ophthalmic substrate in discrete regions or spots on the surface, the amount of surfactant present at or near the surface of the alignment layer can be locally altered. Since alignment of the liquid crystal material applied to the alignment layer will depend, in part, upon the amount of surfactant present at or near the surface of the alignment layer, by locally varying the amount of surfactant present at or near the surface of the alignment layer in this manner, index-change information can be written to the alignment layer. As discussed above, the specific spots on the ophthalmic substrate and the energies employed are determined based on the pattern calculated from the aberrometer measurements, which in turn is based on the prescription information obtained from the patient's eye.

After writing the index-change information to the alignment material of the alignment layer, a liquid crystal material may be applied onto the patterned alignment layer and at least a portion of the liquid crystal mesogens of the liquid crystal material may be allowed to align with the alignment layer. In this manner, the index-change information that was written to the alignment material can be transferred (i.e., written) to the liquid crystal material to create the variable-index coating. After alignment of the liquid crystal material, a setting step may be implemented to lock the liquid crystal alignment in place, for example, by curing, polymerizing, cross-linking, cooling or drying the material as appropriate.

As previously discussed, optionally, a protective coating, such as an abrasion resistant coating may be applied over the variable-index coating. Further, if necessary or desired, a protective tie-layer that provides a hardness gradient between the variable-index coating and the abrasion resistant coating may be applied over the variable-index coating prior to application of the abrasion resistant coating. Further, according to various non-limiting embodiments disclosed herein a second substrate (which may be the same or different from the original substrate) may be positioned over the variable-index coating to form a "sandwich" or "cell" structure. For example, although not limiting herein, a second substrate may be laminated to the original substrate using heat and/or pressure such that the variable-index coating is positioned between the two substrates.

According to various non-limiting embodiments disclosed herein, in addition to the variable-index coating, one or more of the following coatings may be applied to the ophthalmic substrates either before or after forming the variable-index coating on the substrate: anti-reflective coatings, UV absorbing coatings, polarizing coatings, abrasion resistant coatings, tie-layer coatings, tinted coatings, and photochromic coatings. Additionally or alternatively, the variable-index coating may itself comprise one or more additives, such as refractive index enhancing additives, tilt control additives, alignment promoters, adhesion promoters, surfactants (e.g., leveling agents and wetting agents), photochromic dyes, dichroic dyes, color dyes, anti-reflective additives, UV absorbers and other light stabilizers, in addition to the customizable material.

Suitable methods of applying materials to form coatings according to various non-limiting embodiments disclosed herein include, without limitation, spin coating (including both single and multi-layer spin coating), dip coating, in-mold casting and overmolding.

According to one non-limiting embodiment the variable-index coating may be formed on a substrate by overmolding. Referring now to FIG. 1, according to this non-limiting embodiment, a photo-orientation material may be applied to a surface 110 of an ophthalmic substrate 112 (for example a lens or lens blank), by spin coating or other suitable coating method, and either sequentially or simultaneously ordered and cross-linked by scanning a polarized light over the photo-orientation material to create a patterned alignment layer 113 on the surface of the substrate. As previously discussed, by varying the incident angle of the polarization light with respect to the surface of the ophthalmic substrate in discrete regions or spots on the surface, the orientation of the photo-orientation material can be altered in those regions or spots. The specific spots on the substrate and the polarization angles to be used are determined by the pattern calculated from the aberrometer measurements and are based on the prescription information obtained from the patient's eye.

Thereafter, the substrate 112 may be placed adjacent to a mold 116, which may be formed from a material that is transparent to certain wavelengths of electromagnetic radiation, such that at least portion of the alignment layer 113 on surface 110 of ophthalmic substrate 112 is adjacent a surface 114 of mold 116 to define a molding region 117. Surface 114 of mold 116 may be concave or spherically negative (as shown), or it may have another configuration as required to produce the desired coating profile. Further, although not required, a gasket or spacer 115 may be placed between substrate 112 and mold 116. After positioning substrate 112, a customizable material 118 maybe introduced into molding region 117 such that at least a portion of material 118 is caused to flow between substrate 112 and mold 116. At least a portion of material 118 may then be allowed to align with alignment layer 113 to write the index-change information from alignment layer 113 into material 118 to form a variable-index coating. Thereafter, material 118 maybe at least partially set to lock in the index-change information. After setting material 118, substrate 112 comprising the variable-index coating may be removed from the mold.

Although not shown in FIG. 1, in addition to or instead of forming an alignment layer on the surface of the substrate, an alignment layer may be formed on the surface of the mold. For example, a photo-orientation material may be applied to the mold surface and patterned (as previously described) to form an alignment layer. Thereafter, the variable index coating may be formed by introducing the customizable material into the molding region and allowing the material to align with the alignment layer on the mold, and if present, the alignment layer on the substrate.

Alternatively, overmolding may include introducing a customizable material onto the surface of mold prior to placing at least a portion of surface of a substrate adjacent thereto, such that at least a portion of surface of the substrate contacts at least a portion of the customizable material causing the material to flow between the two surfaces. The customizable material may then be allowed to align with an alignment layer on the mold and/or an alignment layer on the substrate to form a variable-index coating. Thereafter, the customizable material may be at least partially set to lock in the index-change information. After setting the customizable material, the substrate comprising the variable-index coating may be removed from the mold.

According to another non-limiting embodiment, an ophthalmic substrate having a variable-index coating may be formed by in-mold casting. According to this non-limiting embodiment, an alignment layer containing index-change information may be formed on the surface of a mold, for example, as described above with respect to the overmolding process. Thereafter, a customizable material may be applied to the alignment layer on the surface of a mold, aligned with the alignment layer to form a variable-index coating, and the material may be at least partially set to lock in the index change information. Thereafter, a polymer solution or melt, or oligomeric or monomeric solution or mixture may be cast in the mold over the variable-index coating, and at least partially set to form the ophthalmic substrate. After setting, the substrate with the variable-index coating may be removed from the mold.

According to still another non-limiting embodiment, an ophthalmic substrate comprising a variable-index coating may be formed between two substrates. According to this non-limiting embodiment, a pair of complementary ophthalmic substrates is formed such that a surface of a first substrate has a curvature complementary to the curvature of a surface of the second substrate. An alignment layer containing index-change information is then formed on either or both of the complementary surfaces. Thereafter, the two substrates are placed together such that their complementary surfaces are facing each other but spaced apart to form a gap between the two surfaces. A customizable material is then introduced into the gap and allowed to align with the alignment layer(s) on the surface(s) to form a variable-index coating. If necessary or desired, spacers may be provided between the substrates so as to ensure the desired gap size and variable-index coating thickness is achieved. Further, if necessary or desired, prior to introducing the customizable material into the gap, an adhesive material may be applied about the perimeter of the complementary substrates provided that at least one opening through which the customizable material may be introduced remains. Thereafter, the customizable material may be at least partially set to lock in the index-change information. Optionally, a sealant may be applied to the edges of the substrates before or after setting the customizable material to form a seal.

Alternatively, according to another non-limiting embodiment, the customizable material may be introduced onto one of the complementary surfaces prior to placing the substrates together. According to this non-limiting embodiment, at least one of the complementary surfaces comprises an alignment layer containing index-change information, and when the substrates are placed together, the customizable material is caused to flow between the complementary surfaces. Thereafter, the customizable material may be aligned with a least a portion of the alignment layer as discussed above. If necessary or desired, spacers or a gasket may be provided between the substrates so as to ensure the desired variable-index coating thickness is achieved. For example, transparent microbeads spacers having a desired diameter may be incorporated into the customizable material prior to or after applying the material to the surface of the substrate and before placing the two substrates together. After alignment, the customizable material may be at least partially set to lock in the index-change information. Optionally, a sealant may be applied to the perimeter of the substrates before or after setting the customizable material to form a seal.

Further, according to various non-limiting embodiments, variable-index film or sheet may be formed and subsequently applied to the substrate, for example, by lamination (with or without the use of an adhesive). For example, according to one non-limiting embodiment, variable-index film or sheet may be formed and thereafter applied to a substrate. According to this non-limiting embodiment, a coating of an alignment material may be applied to a sacrificial substrate or transfer sheet and index-change information may be written to the alignment material as previously described. Thereafter, a liquid crystal material may be applied to the alignment material and allowed to align with alignment material to form a variable-index film or sheet. This film or sheet may then be applied, for example, to an ophthalmic substrate to form a customized ophthalmic element.

According to still other non-limiting embodiments, a variable-index sheet or film can be formed as discussed above and thereafter formed into an ophthalmic element, such as contact lens.

Although not limiting herein, it is contemplated by the inventors that techniques such as overmolding, in-mold casting, forming between substrates and lamination may allow for the formation of thick variable-index layers (for example a variable-index coating, sheet or film) on a substrate, and may therefore be well-suited for applications wherein thick layers, for example layers greater than 30 microns, greater than 50 microns, or layers on the order of 100 microns or more, are preferred.

According to various non-limiting embodiments disclosed herein, the variable-index coating may be applied to a single face of the ophthalmic substrate. According to other non-limiting embodiments disclosed herein, a variable-index coating may be applied to both faces of the ophthalmic substrate. Although not limiting herein, it is contemplated that utilization of both faces of the ophthalmic substrate may allow a greater thickness in which to write index-change information, thereby permitting manufacture of a wider variety of customized elements.

Other non-limiting embodiments disclosed herein provide a customized ophthalmic element comprising an ophthalmic substrate and an variable-index coating comprising a liquid crystal material that has well defined variations in refractive index meeting customer specific lens prescription needs connected to the ophthalmic substrate. According to one non-limiting embodiment, the variable-index coating may be an at least partial coating adapted to contain variations in refractive index throughout the coating configured to eliminate higher order aberrations. According to another non-limiting embodiment, the variable-index coating may contain variations in focal points that are configured to produce a smooth-faced bifocal lens or a progressive addition lens. For example, as shown in FIG. 3, the liquid crystal material may be patterned to create a smooth-faced bifocal lens (left) that is functionally equivalent to the conventional bifocal lens shown (right). According to still another non-limiting embodiment, the variable-index coating may be an at least partial coating adapted to contains variations in refractive index designed to eliminate higher order aberrations and to produce a smooth-faced bifocal or a progressive addition lens.

Another non-limiting embodiment provides a customized ophthalmic element comprising an ophthalmic substrate and a variable-index layer, e.g., a coating, comprising a liquid crystal material connected to at least a portion of the substrate. According to this non-limiting embodiment, the ophthalmic element may further comprise an alignment layer that is interposed between and connected to each of the ophthalmic substrate and the variable-index layer, e.g., a coating. Further, according to this non-limiting embodiment, the ophthalmic substrate may be a single or multi-vision lens or a contact lens. As used herein the term "connected to" means in direct contact with an object, such as an ophthalmic substrate, or indirect contact with an object through one or more other structures or materials, or layers, at least one of which is in direct contact with the object. Thus, according to various non-limiting embodiments disclosed herein, the variable-index layer or coating can be in direct contact with at least a portion of the substrate or it can be in indirect contact with at least a portion of the substrate through one or more other structures or materials. For example, although not limiting herein, the variable-index coating can be in contact with one or more other at least partial layers, coatings, sheets or films, or combinations thereof, at least one of which is in direct contact with at least a portion of the substrate.

Another non-limiting embodiment provides a customized ophthalmic element comprising an ophthalmic substrate and a variable-index layer in the form of a sheet or film comprising a liquid crystal material connected to at least a portion of the substrate. According to this non-limiting embodiment, the ophthalmic element may further comprise an alignment layer that is interposed between and connected to each of the ophthalmic substrate and the variable-index sheet or film. Further, according to this non-limiting embodiment, the ophthalmic substrate may be a single or multi-vision lens or a contact lens.

Another non-limiting embodiment provides a customized ophthalmic element comprising an ophthalmic substrate, an alignment layer comprising an at least partial coating of an at least partially aligned alignment material connected to at least of portion of the ophthalmic substrate, and a variable-index coating comprising a liquid crystal material connected to the alignment layer, wherein at least a portion of the liquid crystal material of the variable-index coating is aligned with at least a portion of the alignment material. Although not required, according this non-limiting embodiment, the alignment material may be a photo-orientation material, such as, but not limited to, a photo-orientable polymer network material. Further, according to this non-limiting embodiment, the ophthalmic substrate may be a single or multi-vision lens or a contact lens.

Still another non-limiting embodiment disclosed herein provides an ophthalmic element comprising a pair of complementary ophthalmic substrates, each of the substrates having a complementary surface, the pair of complementary ophthalmic substrates being positioned such that their complementary surfaces that are spaced apart and facing each other, an alignment layer comprising an at least partial coating of a patterned alignment material connected to at least of portion of at least one of the complementary surfaces of the pair of ophthalmic substrates, and an variable-index coating comprising a liquid crystal material that is interposed between the pair of ophthalmic substrates, wherein at least a portion of the liquid crystal material of the variable-index coating is aligned with at least a portion of the patterned alignment material.

Although not required, according to one non-limiting embodiment, the alignment material may be a photo-orientation material, such as, but not limited to, a photo-orientable polymer network material.

Aspects of the disclosure are illustrated below in the following, non-limiting example.

EXAMPLE

A variable-index coating was formed on a substrate from CR-39® monomer as follows. A photo-orientation material, Staralign 2100 CP solution available from Vantico, was applied to the substrate and a concentric square pattern was written to the photo-orientation material using polarized UV light and masks (as described hereafter) to form an alignment layer on the substrate. The inner square of the pattern was written to the photo-orientation material by masking the outer square region and then ordering the exposed inner square region using perpendicularly-incident polarized UV. The inner square region was then masked, and the outer square pattern was written to the photo-orientation material by ordering the exposed outer square region using polarized UV applied at a grazing angle with respect to the wafer surface.

Thereafter, a solution of liquid crystal monomers, RM 257 and RM 105, which are available from EMD Chemicals (Merck KGaA, Germany), in anisole was spun on to the alignment layer to form a coating. The liquid crystal monomers were then allowed to align with the pattern that was written to the photo-orientation material using the polarized UV radiation in order to transfer (i.e., write) the concentric square pattern from the photo-orientation material to the liquid crystal monomer coating to create the variable-index coating. The sample was then cured with UV radiation to lock in the alignment of the liquid crystal monomers.

Evidence of an index of refraction difference between the two concentric square regions written to the variable-index coating was observed when the sample was viewed over a grid pattern. A square pattern of distortion was evident at the border between the concentric square regions, indicating a difference in refractive index between the two regions.

It is to be understood that the present description illustrates aspects of the invention relevant to a clear understanding of the invention. Certain aspects of the invention that would be apparent to those of ordinary skill in the art and that, therefore, would not facilitate a better understanding of the invention have not been presented in order to simplify the present description. Although the present invention has been described in connection with certain embodiments, the present invention is not limited to the particular embodiments disclosed, but is intended to cover modifications that are within the spirit and scope of the invention.

We claim:

1. A customized ophthalmic element comprising an ophthalmic substrate; a variable-index layer comprising an at least partially set liquid crystal material connected to at least a portion of the substrate, and an alignment layer comprising an alignment material containing index-change information interposed between and connected to each of the ophthalmic substrate and the variable-index layer comprising a liquid crystal material, wherein at least a portion of the liquid crystal material of the variable-index layer is aligned with at least a portion of the alignment material.

2. The customized ophthalmic element of claim 1, wherein the substrate comprises a single-vision lens, a multi-vision lens, or a contact lens.

3. The customized ophthalmic element of claim 1, wherein the variable-index layer is in the form of a coating comprising a liquid crystal material.

4. The customized ophthalmic element of claim 1, wherein the variable-index layer is in the form of a sheet or film comprising a liquid crystal material.

5. An ophthalmic element comprising a pair of complementary ophthalmic substrates, each of the substrates having a complementary surface, the pair of complementary ophthalmic substrates being positioned such that their complementary surfaces that are spaced apart and facing each other, an alignment layer comprising an at least partial coating of a patterned alignment material containing index-change information connected to at least of portion of at least one of the complementary surfaces of the pair of ophthalmic substrates, and a variable-index coating comprising an at least partially set liquid crystal material that is interposed between the pair of ophthalmic substrates, wherein at least a portion of the liquid crystal material of the variable-index coating is aligned with at least a portion of the patterned alignment material.

* * * * *